United States Patent [19]

Delaney

[11] Patent Number: 5,149,354
[45] Date of Patent: Sep. 22, 1992

[54] COMPOSITION FOR TREATING SWIMMING POOLS

[76] Inventor: Brendan J. Delaney, 68 Honiball Street, Rynfield, Benoni, South Africa

[21] Appl. No.: 639,800

[22] Filed: Jan. 10, 1991

[51] Int. Cl.$^5$ .................. A01N 25/08; A01N 59/20; A01N 59/16

[52] U.S. Cl. ..................... 71/67; 514/495; 514/500

[58] Field of Search .................. 71/67; 514/495, 500

[56] References Cited

U.S. PATENT DOCUMENTS

| | | | |
|---|---|---|---|
| 2,400,863 | 5/1946 | Gelfand | 71/67 |
| 3,296,069 | 1/1967 | Kowalski | 71/67 |
| 3,930,834 | 1/1976 | Schulteis et al. | 71/67 |
| 4,931,078 | 6/1990 | Yamamoto | 71/67 |

FOREIGN PATENT DOCUMENTS

2579972  4/1986  France .
2158060  11/1985  United Kingdom .

*Primary Examiner*—Richard Raymond
*Assistant Examiner*—S. Mark Clardy
*Attorney, Agent, or Firm*—Kuhn and Muller

[57] ABSTRACT

A composition for treating swimming pools to inhibit the growth of algae, fungi and bacteria, and to prevent the formation of turbidity in the pool water, more particularly to reduce the dosage of chlorine or chlorine-based chemicals to maintain the pool water in a clear and pathogen-free condition, while at the same time substantially eliminating the risk of deposits and stains being formed on the pool walls, comprises by weight:
  from about 78 to about 83 percent of copper sulphate,
  from about 0.08 to about 0.12 percent of silver nitrate,
  from about 1.0 to about 1.4 percent each of sodium gluconate and zinc chloride or zinc sulphate,
from about 16.4 to about 9.6 percent of water, and from about 3.5 to about 4.5 of a complexone, preferably the tetrasodium salt of EDTA.

To ensure the desired properties and consistency of the product as well as successful manufacture, the ingredients have to be mixed in a particular manner and sequence of steps.

27 Claims, 1 Drawing Sheet

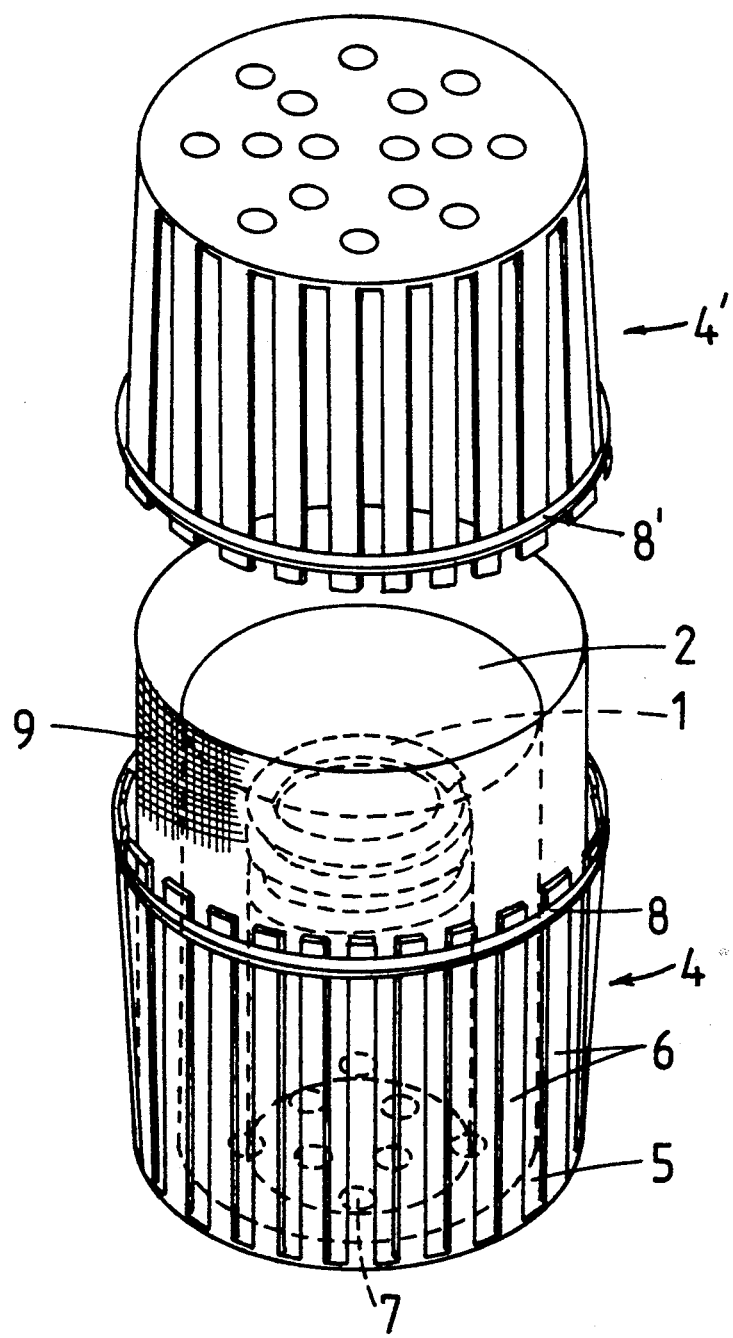

COMPOSITION FOR TREATING SWIMMING POOLS

FIELD OF THE INVENTION

The present invention relates to a composition for treating swimming pools, particularly to inhibit the growth of algae, fungi and bacteria therein, and to prevent the formation of turbidity in the swimming pool water. More particularly the invention provides a composition the use of which reduces the dosage of chlorine or chlorine- or hypochlorite-forming or -releasing agents to maintain the pool water in a clear and pathogen-free condition, while at the same time substantially eliminating the risk of deposits and stains being formed on the walls of the pool.

BACKGROUND OF THE INVENTION

Swimming pool water, in order to maintain it in a clear and pathogen-free condition, needs regular treatment with appropriate pool chemicals or chemical compositions. For many decades, chlorine gas (for public swimming pools, for example) and chlorine- or hypochlorite-releasing agents such as $Ca(OH)_2/Ca(OCL)_2$ and trichloroisocyanuric acid or its salts (for private swimming pools) have been the favoured agents. Many devices have also come on the market which produce chlorine in the water circulation system of a pool by electrolysis, e.g. of HCL or NaCL solutions.

Despite the beneficial effects thereof in pool disinfection, the use of chlorine and chlorine-based products suffers from a number of disadvantages. The hypochlorous acid formed by hydrolysis of $Cl_2$ is rapidly destroyed by sunlight (K. Wehrmann and F. Zobrist, Schweiz. Z. Hydrol. 20, 218, 1958). This disadvantage has led to the introduction of the trichloroisocyanurates as stabilizers.

Hypochlorous acid and chloride ions interact with organic matter from vegetable matter falling into pools, and with urine, perspiration and sun-tan oils from swimmers, to give various chlorinated products, one type of which, the chloramines, produces irritation of the eyes. Over the past decade or two these chlorinated products have been recognised as a health hazard (J. A. Beech et al., Amer. J. Public Health 70, 79, 1980). Thus the ingestion of these chlorinated hydrocarbons has been directly linked to stomach cancer, and a maximum of 100 p.p.b. has been recommended for potable water (J. A. Borchardt et. al., "Viruses and Trace Contaminants in Water and Waste Water", Ann Arbor Science, Michigan, 1977). L. Schou and H. Oedegaard (Miljoevardsserein 1, 277, 1981) have shown that this level is easily exceeded in many swimming pools, and there is the suspicion that absorption of these carcinogenic compounds through the skin, particularly with infants, may exceed tolerable levels.

Since the amounts of chlorinated hydrocarbons observed increase with the quantity of chlorine used, it is obviously desirable to reduce the application rate or dosage of chlorine or chlorine-based chemicals. Another incentive is the rising costs of these chemicals, and the fact that chlorine, an oxidising agent, reacts with dyes, resulting in discoloration, and eventually bleaching, of swimwear. They also attack cotton and elasticized materials in swimwear and the vinyl liners of pools. Furthermore, since chlorine is only effective over a narrow pH range, the use of chlorine in a swimming pool requires regular pH-corrective steps.

To reduce the amount of chlorine or chlorine-based chemicals needed to maintain swimming pools in a clear and substantially pathogen-free state, many variants of chemical compositions have been proposed and introduced into the market during the past two or three decades. These act mainly to destroy and/or inhibit the growth of algae and bacteria, the destruction of algae and bacteria being otherwise responsible for a major part of the consumption of chlorine. (It is to be noted, however, that the use of chlorine or chlorine-based chemicals cannot, in general, be dispensed with entirely, for the destruction of viruses and certain other pathogens still requires the use of a strong oxidising agent, for which chlorine is still regarded as the most efficient and cost-effective, and the safest.)

These compositions generally incorporate polymeric compounds containing quaternary ammonium compounds (for example, WSCP ® of Buckman Laboratories, Michigan, USA, the chemical composition of which is given as poly [oxyethylene (dimethylimino)ethylene(dimethylimino)ethylene dichloride]) and/or heavy metal ions such as $Cu^{2+}$, $Ag^+$, $Zn^{2+}$, $Sn^{2+}/Sn^{4+}$, $Ni^{2+}$ and $Hg^{2+}$, preference being give to $Cu^{2+}$ and $Ag^+$. Other compositions (e.g. South African Patent 78/2234 to D. M. Rice) contain a $Cu^{2+}$ salt and potassium iodide, which react in water to give free iodine. It is believed that the cuprous iodide produced in the reaction is reoxidised by the dissolved oxygen in the water to $Cu^{2+}$, which will then reoxidise the iodide ions formed in the disinfectant action of the $I_2$. The $Cu^{2+}$ ions also act as an algicide.

$Cu^{2+}$ and $Ag^+$ and other ions with bactericidal and algicidal properties may for example be continuously generated in a pool by electrolysis using Ag/Cu sacrificial electrodes, or by the use of sparingly soluble salts. Soluble salts may also be administered by dosing devices.

The use of particularly $Cu^{2+}$ and $Ag^+$ has a number of advantages, including the low concentrations required, the provision of a long-lasting residual effect, easy handling, their low toxicity and tastelessness at the concentrations used, and the fact that sunlight has only a minor effect on their action.

However, they suffer from a number of disadvantages:

(a) They tend to give rise to a slight turbidity.
(b) The presence of appreciable concentrations of chloride and sulphate ions in the pool water limits their effectiveness.
(c) The metal ions have a tendency to undergo precipitation, leading particularly to the staining of the pool walls.
(d) The metal ions tend to plate out on the iron metal parts of the filtration and circulation equipment, with the concomitant formation of a fine, red-brown precipitate of ferric hydroxide, particularly when $Cu^{2+}$ is used in the highest concentration ranges.

A composition used on the South African market under the trade name "Pool Wizard" since about 1983 has been successful in reducing the pool chlorine dosage. This solid composition comprises copper sulphate, silver nitrate, zinc sulphate and sodium gluconate, cast over a coil of copper wire, all provided in a small cage-like basket, serving as a dispenser, placed in the leaf trap of a pool circulation system. The solid dissolves up in the circulation water within about 30 minutes. The action of one such unit of the composition is claimed to last for 9 to 12 months, and to reduce the chlorine dosing requirement immediately by 50 percent, with a gradual further reduction of up to a total of 75 percent.

However, this composition still suffers from the disadvantages (c) and (d) enumerated above, and many complaints have been received by the manufacturers, with which the present inventor and applicant is associated, of unsightly stains forming on the walls of pools treated with this composition. The formation of a turbidity also presents problems.

There is therefore a need to improve compositions of the type containing particularly $Cu^{2+}$ as one of the major bacterides/algicides, to eliminate the problems due to pool-wall staining and the disadvantages described under (d) above.

Another problem that has been encountered in the compounding of compositions for swimming pool treatment comprising heavy metal ions, especially when using unskilled staff, is the frothing of the mixture and/or the formation of black deposits (which do not readily redissolve) when the ingredients are mixed together.

OBJECTS OF THE INVENTION

An object of the present invention is to provide an improved composition for treating swimming pool water, the use of which reduces the required chlorine dosage of a swimming pool while at the same time substantially eliminating the risk of the formation of turbidity in the pool water and of staining of the pool walls, as well as substantially eliminating the attack of $Cu^{2+}$ ions on the iron metal parts of the filtration and circulation equipment.

Another object of the invention is to provide a process for compounding the composition of the invention, which eliminates the problems due to frothing and the formation of deposits previously encountered.

SUMMARY OF THE INVENTION

It has now been found surprisingly that the staining of the walls of a swimming pool and attacks on the iron metal parts of the filtration and circulation equipment of a swimming pool, when using a pool treatment composition of the prior art type containing heavy metal ions, may be susbtantially prevented or eliminated by the incorporation into the composition, in addition to the heavy metal compound ingredients, of a suitable complexone.

Thus in accordance with one aspect of the invention there is provided a solid bactericidal, algicidal and fungicidal composition for use in the treatment of the water of a swimming pool to reduce the swimming pool chlorine dosage requirement, comprising:

I. a mixture of active ingredients comprising by weight
   a) a water-soluble copper compound, serving as a source of copper ion, representing, calculated as $CuSo_4 \cdot 5H_2O$, more than 50% of all active ingredients,
   b) a water-soluble silver compound capable of supplying a bactericidal concentration of silver ion,
   c) a water-soluble gluconate capable of forming soluble complexes with silver,
   d) a complexone, capable of forming water-soluble copper complexes in an amount of about between 1/50 and 1/5 of the amount of said copper compound, calculated as $CuSo_4 \cdot 5H_2O$,
   e) between about 5 and 30% water, and II. a copper reactivator means, comprising solid copper, III. the composition being a solid form suitable for placing in a dispenser having water pervious walls.

The preferred composition in addition comprises from about 1 to 3 percent by weight of a water-soluble zinc salt, calculated as $ZnSo_4 \cdot 7H_2O$, and preferably in the form of zinc chloride or sulphate.

The complexone is preferably ethylenediaminetetraacetic acid (EDTA) or a suitable alkali metal salt thereof, for example the disodium or the tetrasodium salt.

In a preferred composition the mixture comprises by weight:

from about 78 to about 83 percent, preferably 80 to 81 percent of copper sulphate (as $CuSo_4 \cdot 5H_2O$), from about 0.08 to about 0.12 percent, of silver nitrate, preferably about 0.10 percent, from about 1.0 to about 1.4 percent, preferably about 1.2 percent, of sodium gluconate, from about 1.0 to about 1.4 percent, perferably about 1.2 percent, of zinc chloride or zinc sulphate (as $ZnSO_4 \cdot 7H_2O$), from about 16.4 to about 9.6 percent, preferably about 13 percent, of water, and from about 3.5 to about 4.5 percent, preferably about 4 percent, of the complexone, preferably the tetrasodium salt of ethylenediaminetetraacetic acid.

In the applicant's experience the manner by which the composition is produced constitutes an important factor which in a manner not fully understood by the applicant decides the properties and consistency of the product, as a firm, solid block, as well as the successful manufacture.

It was found that unless the manufacture is conducted substantially in a particular manner and sequence of steps, the components interact in manners not leading to the desired product. In particular one result consistently observed has been uncontrollable frothing and the formation of black solid deposits, rendering orderly manufacture quite impossible. As a result of extensive experimentation these problems were surprisingly overcome completely.

Thus the invention further teaches a process of preparing a composition as aforesaid, which comprises first preparing a hot solution of the components of (I) b), c) and e), and optionally a minor fraction of component I d), then adding to that solution with agitation progressively and gradually in alternating increments or concurrently the components a) and d) to form a paste, and casting the paste into blocks which solidify on cooling, said blocks incorporating or being each closely associated with a copper reactivator means, comprising solid copper.

Advantageously the process further comprises incorporating from about 1 to about 3 percent by weight of a water-soluble zinc salt, calculated as $ZnSO_4 \cdot 7H_2O$, in the hot solution prior to the adding of components (I) a) and d).

The preferred process comprises the steps of:
(a) placing the entire water component in a suitable container, and heating to boiling;
(b) while boiling, adding the entire sodium gluconate and zinc sulphate or zinc chloride components to the boiling water, and agitating to dissolve;
(c) with boiling and agitating, adding a portion of the copper sulphate and the entire component of silver nitrate, followed by a portion of the complexone;

(d) with boiling and agitating, adding alternately and successively further portions of copper sulphate and a complexone, until the entire copper sulphate and complexone components have been added and dispersed and/or dissolved; and (e) pouring the resulting paste into suitable molds, and allowing the paste to solidify.

In practice the increments in which the portions of copper sulphate and complexone are added to the solution preferably each represent less than 10% by weight of the total of each said component, e.g. about 5% by weight. However, it will be understood that the additions may proceed in smaller increments and that this will ultimately, if the increments are very small, be equivalent to progressively and gradually, i.e. very slowly, say over a period of about an hour or even longer, adding the two components concurrently.

The solid composition for treating swimming pools according to the invention is normally provided in a dispenser, in which the composition may be dissolved away by the circulating pool water when the dispenser is in the water circulation system of the pool, placed for example in the leaf trap of the pool. No special requirements have to be met by the dispenser, other than that its walls must be sufficiently pervious for water readily to flow therethrough. Dispensers of this type are in various forms known in the art.

BRIEF DESCRIPTION OF THE DRAWING

The drawing, in an exploded view, merely illustrates an example of a dispenser suitable for use with the composition of the invention.

SPECIFIC EMBODIMENTS OF THE INVENTION

A composition for treating swimming pools in accordance with the invention typically comprises the following ingredients, given in percentage by weight (with the quantities given in brackets denoting the weights of the ingredients required to make up 124.125 kg of the composition, in a batch sufficient to prepare 350 block units ready for application):

80.56 percent (100 kg) of copper sulphate ($CuSO_4 \cdot 7H_2O$),
0.10 percent (125 g) of silver nitrate,
1.21 percent (1,5 kg) of sodium gluconate,
1.21 percent (1,5 kg) of zinc sulphate ($ZnSO_4 \cdot 7H_2O$),
4.02 percent (5 kg) of Trilon B ®, and
12.90 percent (16 kg) of water, wherein Trilon B is the trade name of tetrasodium salt of EDTA (ethylenediaminetetraacetic acid), as supplied by BASF South Africa (Pty) Ltd.

The composition is made up by placing the water component in a suitable tank and adding the ingredients in the following order with stirring and while keeping the mixture boiling, taking care to ensure that each portion is fully dissolved and/or dispersed before the next portion is added. First, all of the sodium gluconate and zinc sulfate is added. This is followed by about 5 kg of copper sulphate. All of the silver nitrate is then added, then another 5 kg of copper sulphate, followed by 1 kg of Trilon-B. Portions of copper sulphate and Trilon-B are now added alternately, until all has been added. The mixture, which by now is a paste, is heated with stirring for about 30 min., while keeping it on the boil. The mixture is then poured into frusto-conical molds (e.g. of 175 ml capacity) and allowed to cool and solidify, to form "blocks" of the composition.

The composition of the invention requires, for its proper functioning, a copper metal reactivator means exposed to the circulating pool water after the composition has fully dissolved. The copper metal reactivator means may be supplied and installed separately in the circulating pool water. Alternatively the copper metal, in the form of copper wire, for example stranded 4 mm copper wire (as used in earthing cables), provided in the form of a coil, may be fitted around the block of the composition inside the dispenser (illustrated in FIG. 1).

Alternatively and preferably, a coil of stranded copper wire (of weight for example about 200 g) is placed in the mold before the heated paste comprising the composition of the invention is poured into the mold, thereby producing a block of the composition with the copper metal reactivator incorporated in the block. This preferred embodiment thereby obviates separate handling and installment of the copper metal reactivator.

In the drawing, the block 2 of the composition in accordance with the invention, with the copper metal reactivator means shown in broken lines 1 entrapped therein has been placed in one half of a cage-like dispenser 4 the sidewalls of which comprise a plurality of ribs 6, with longitudinal openings 5 between them, the end surface of the dispenser containing a plurality of holes 7, etc.

The other half 4' of the dispenser is essentially identical to the first half 4. During assembly of the dispenser it is fitted on to the first half 4, to form a closed dispenser or basket, housing the block 2 therein. For that purpose the rims 8 and 8' of the two halves have complementary interengaging slip or screw formations. Optionally a sieve 9 of plastic gauze is provided between the block 2 and the screen wall of the basket 4, 4'.

What is claimed is:

1. A bactericidal, algicidal and fungicidal composition for use in the treatment of the water of a swimming pool comprising
I. a mixture of active ingredients comprising by weight
   a) a water-soluble copper compound, serving as a source of copper ion, representing, calculated as $CuSO_4 \cdot 5H_2O$, more than 50% of all active ingredients,
   b) a water-soluble silver compound capable of supplying a bactericidal concentration of silver ion,
   c) a water-soluble gluconate capable of forming soluble complexes with silver,
   d) a complexone, being an organic amine capable of forming water-soluble copper complexes in an amount of about between 1/50 and 1/5 of the amount of said copper compound, calculated as $CuSO_4 \cdot 5H_2O$,
   e) between about 5 and 30% water, and
II. a copper reactivator means, comprising solid copper metal,
III. the composition being a solid form suitable for placing in a dispenser having water pervious walls.

2. A composition as claimed in claim 1, wherein (I) further comprises f) from about 1 to about 3 percent by weight of a water-soluble zinc salt, calculated as $ZnSO_4 \cdot 7H_2O$.

3. A composition as claimed in claim 1, wherein the complexone is selected from the group consisting of ethylenediaminetetraacetic acid (EDTA) and the alkali metal salts thereof.

4. A composition as claimed in claim 3, wherein the complexone is the disodium or the tetrasodium salt of EDTA.

5. A composition as claimed in claim 1, prepared by first preparing a hot solution of the components of (I) b), c) and e), and optionally a minor fraction of component (I) d), then adding to that solution with agitation progressively and gradually in alternating increments or concurrently the components a) and d) to form a paste, and casting the paste into blocks which solidify on cooling.

6. A composition according to claim 1, wherein the mixture (I) of active ingredients is composed by weight as follows:
 a) from 78 to about 83 percent of copper sulphate (as $CuSO_4 \cdot 5H_2O$),
 b) from about 0.08 to about 0.12 percent of silver nitrate,
 c) from about 1.0 to about 1.4 percent of sodium gluconate,
 d) from about 3.5 to about 4.5 percent by weight of the complexone,
 e) from about 16.4 to about 9.6 percent of water, and
 f) from about 1.0 to about 1.4 percent of zinc chloride or zinc sulphate (as $ZnSO_4 \cdot H_2O$).

7. A composition as claimed in claim 1, wherein the mixture (I) comprises by weight:
about 80-81 percent of copper sulphate ($CuSO_4 \cdot 5H_2O$),
about 0.1 percent of silver nitrate,
about 1.2 percent of sodium gluconate,
about 1.2 percent of zinc sulphate ($ZnSO_4 \cdot 7H_2O$),
about 4 percent of the tetrasodium salt of ethylenediaminetetraacetic acid, and
about 13 percent of water.

8. A composition as claimed in claim 6, prepared by the steps of:
 (i) placing the entire water component (I) e) in a suitable container, and heating to boiling;
 (ii) while boiling, adding the entire sodium gluconate (I) c) and zinc sulphate or zinc chloride components (I) f) to the boiling water, and agitating to dissolve;
 (iii) with boiling and agitation, adding a fractional portion of the copper sulphate and the entire component of silver nitrate, followed by a fractional portion of the complexone, proportionate to the fractional portion of copper sulphate;
 (iv) with boiling and agitation, adding alternately and successively further proportionate portions of copper sulphate and the complexone, until the entire copper sulphate and complexone components have been added and dispersed and/or dissolved; and
 (v) pouring the resulting paste into suitable molds, and allowing the paste to solidify.

9. A composition as claimed in claim 8, wherein the copper metal reactivator means is incorporated in blocks of the composition.

10. A composition as claimed in claim 1, enclosed in a dispenser of plastics material forming a cage-like structure through which water can flow freely.

11. A process of preparing a composition as claimed in claim 1, which comprises first preparing a hot solution of the components of (I) b), c) and e), and optionally a minor fraction of component I (d), then adding to that solution with agitation progressively and gradually in alternating increments or concurrently the components a) and d) to form a paste, and casting the paste into blocks which solidify on cooling, said blocks incorporating or being each closely associated with a copper reactivator means, comprising solid copper.

12. A process as claimed in claim 11, which further comprises incorporating from about 1 to about 3 percent by weight of a water-soluble zinc salt, calculated as $ZnSO_4 \cdot 7H_2O$, in the hot solution prior to the adding of components (I) a) and d).

13. A process as claimed in claim 11, which comprises the steps of:
 (i) placing the entire water component (I) e) in a suitable container, and heating to boiling;
 (ii) while boiling, adding the entire sodium gluconate (I) c) and zinc sulphate or zinc chloride components (I) f) to the boiling water, and agitating to dissolve;
 (iii) with boiling and agitation, adding a fractional portion of the copper sulphate and the entire component of silver nitrate, followed by a fractional portion of the complexone, proportionate to the fractional portion of copper sulphate;
 (iv) with boiling and agitation, adding alternately and successively further proportionate portions of copper sulphate and the complexone, until the entire copper sulphate and complexone components have been added and dispersed and/or dissolved; and
 (v) pouring the resulting paste into suitable molds, and allowing the paste to solidify.

14. A bactericidal, algicidal and fungicidal composition for use in the treatment of the water of a swimming pool, comprising:
I) a mixture of active ingredients comprising by weight:
 a) a water-soluble copper compound, serving as a source of copper ion, representing, calculated as $CuSO_4 \cdot 5H_2O$, more than 50% of all active ingredients;
optionally by lesser amounts of further bactericidal, algicidal and fungicidal ingredients, selected from the group consisting of:
 b) water-soluble zinc and silver compounds and mixtures of both, the silver compound or compounds, if present, being accompanied by
 c) a complexing agent for silver;
the composition further comprising:
 d) a complexone, being an organic amine, capable of forming water-soluble copper complexes, in an amount of between 1/50 and 1/5 of the amount of said copper compound, calculated as $CuSO_4 \cdot 5H_2O$; and
 e) from about 5 to about 30% water;
said composition having been cast in a hot fluid condition and been allowed to set in the form of a solid block.

15. A composition according to claim 14, further comprising:
a copper reactivator means, comprising solid copper, said composition being a solid form suitable for placing in a dispenser having water pervious walls.

16. A composition as claimed in claim 14, wherein said further bactericidal, algicidal and fungicidal ingredients comprise f) from about 1 to about 3 percent by weight of a water-soluble zinc salt, calculated as $ZnSO_4 \cdot 7H_2O$.

17. A composition as claimed in claim 14, wherein said complexone is selected from the group consisting of ethylenediaminetetraacetic acid (EDTA) and the alkali metal salts thereof.

18. A composition as claimed in claim 17, wherein said complexone is the disodium or the tetrasodium salt of EDTA.

19. A composition as claimed in claim 14, prepared in sequential order by first preparing a hot solution of said components of (I) b), c) and e), and optionally a minor fraction of component (I) d), then adding to that solution with agitation progressively and gradually in alternating increments or concurrently said components a) and d) to form a paste, and casting said paste in a hot fluid condition into blocks which solidify on cooling.

20. A composition according to claim 14, wherein said mixture (I) of active ingredients is composed by weight as follows:
   a) from 78 to about 83 percent of copper sulphate (as $CuSO_4 \cdot 5H_2O$,
   b) from about 0.08 to about 0.12 percent of silver nitrate,
   c) from about 1.0 to about 1.4 percent of sodium gluconate,
   d) from about 3.5 to about 4.5 percent by weight of said complexone,
   e) from about 16.4 to about 9.6 percent of water, and
   f) from about 1.0 to about 1.4 percent of zinc chloride or zinc sulphate (as $ZnSO_4 \cdot H_2O$).

21. A composition as claimed in claim 14, wherein said mixture (I) comprises by weight:
   about 80–81 percent of copper sulphate ($CuSO_4 \cdot 5H_2O$),
   about 0.1 percent of silver nitrate,
   about 1.2 percent of sodium gluconate,
   about 1.2 percent of zinc sulphate ($ZnSO_4 \cdot 7H_2O$),
   about 4 percent of the tetrasodium salt of ethylenediaminetetraacetic acid, and
   about 13 percent of water.

22. A composition as claimed in claim 20, prepared in sequential order by the steps of:
   (i) placing said entire water component (I) e) in a suitable container, and heating to boiling;
   (ii) while boiling, adding said entire sodium gluconate (I) c) and zinc sulphate or zinc chloride components (I) f) to said boiling water, and agitating to dissolve;
   (iii) with boiling and agitation, adding a fractional portion of said copper sulphate and said entire component of silver nitrate, followed by a fractional portion of said complexone, proportionate to the fractional portion of copper sulphate;
   (iv) with boiling and agitation, adding alternately and successively further proportionate portions of copper sulphate and said complexone, until said entire copper sulphate and complexone components have been added and dispersed and/or dissolved; and
   (v) pouring said resulting paste in a hot fluid condition into suitable molds, and allowing said paste to solidify.

23. A composition as claimed in claim 22, wherein said copper metal reactivator means is incorporated in blocks of said composition.

24. A process of preparing a composition as claimed in claim 14, which comprises, in sequential order, first preparing a hot solution of said components of (I) b) c) and e), and optionally a minor fraction of component I d), then adding to that solution with agitation progressively and gradually in alternating increments or concurrently said components a) and d) to form a paste, and casting said paste in a hot fluid condition into blocks which solidify on cooling, said blocks incorporating or being each closely associated with a copper reactivator means, comprising solid copper.

25. A process as claimed in claim 24, which further comprises incorporating from about 1 to about 3 percent by weight of a water-soluble zinc salt, calculated as $ZnSO_4 \cdot 7H_2O$, in said hot solution prior to the adding of components (I) a) and d).

26. A process as claimed in claim 24, which comprises in sequential order the steps of:
   (i) placing said entire water component (I) e) in a suitable container, and heating to boiling;
   (ii) while boiling, adding said entire sodium gluconate (I) c) and zinc sulphate or zinc chloride components (I) f) to said boiling water, and agitating to dissolve;
   (iii) with boiling and agitation, adding a fractional portion of said copper sulphate and said entire component of silver nitrate, followed by a fractional portion of said complexone, proportionate to said fractional portion of copper sulphate;
   (iv) with boiling and agitation, adding alternately and successively further proportionate portions of copper sulphate and said complexone, until said entire copper sulphate and complexone components have been added and dispersed and/or dissolved; and
   (v) pouring said resulting paste in a hot fluid condition into suitable molds, and allowing said paste to solidify.

27. A bacteriological, algicidal and fungicidal composition for treating water for swimming pools, comprising in combination:
   I) a mixture of active ingredients comprising by weight:
      a) a water soluble copper compound, serving as a source of copper ion, representing, calculated as $CuSO_4 \cdot 5H_2O$, more than 50% of all active ingredients;
   optionally by lesser amounts of further bacteriological, algicidal, and fungicidal ingredients, selected from the group consisting of:
      b) water-soluble zinc and silver compounds and mixtures of both, the silver compound or compounds, if present, being accompanied by
      c) a complexing agent for silver;
   the composition further comprising:
      d) a complexone, being an organic amine, capable of forming water-soluble copper complexes, in an amount of between 1/50 and 1/5 of the amount of said copper compound, calculated as $CuSO_4 \cdot 5H_2O$, and
      e) from about 5 to about 30% water;
   II) a copper reactivator means, comprising solid copper metal, said copper reactivator means exposable within said pool water;
   III) the composition being a solid form suitable for placement within said pool water for dissolving within said pool water; said composition prepared in a process according to the following steps in sequential order:
      i) placing said entire water component (I) e) in a suitable container, and heating to boiling;
      ii) while boiling, adding said complexing agent for silver and said water-soluble zinc and silver compounds to said boiling water, nd agitating to dissolve;
      iii) with boiling and agitation, adding a fractional portion of said water soluble copper compound and said water-soluble silver compound, followed by said complexone, said complexone being added proportionate to said copper compound;

iv) with boiling and agitation, adding alternatively and successively further proportionate portions of said water-soluble copper compound and said complexone, until said entire water-soluble copper compound and complexone components have been added and dispersed and/or dissolved; and v) pouring said resultant paste in a hot fluid condition into suitable molds, and allowing said paste to solidify.

* * * * *